US00PP25794P2

(12) United States Plant Patent
Vinson

(10) Patent No.: US PP25,794 P2
(45) Date of Patent: Aug. 11, 2015

(54) ***FRAGARIA* PLANT NAMED 'VERITY'**

(50) Latin Name: *Fragaria×ananassa*
Varietal Denomination: Verity

(71) Applicant: Peter Edward Vinson, Kent (GB)

(72) Inventor: Peter Edward Vinson, Kent (GB)

(73) Assignee: EDWARD VINSON LIMITED, Kent (GB)

( * ) Notice: Subject to any disclaimer, the term of this patent is extended or adjusted under 35 U.S.C. 154(b) by 99 days.

(21) Appl. No.: 13/998,803

(22) Filed: Dec. 10, 2013

(51) Int. Cl.
*A01H 5/00* (2006.01)

(52) U.S. Cl.
USPC ..... Plt./209

(58) Field of Classification Search
USPC ..... Plt./209, 208
See application file for complete search history.

*Primary Examiner* — Annette Para
(74) *Attorney, Agent, or Firm* — Penny J. Aguirre

(57) ABSTRACT

A new and distinct day-neutral cultivar of strawberry plant named 'Verity' that is characterized by its upright dense growth habit, its ovoid shaped berries that are uniformly large in size, its berries with firm skin and juicy, soft flesh, its berries that are glossy and bright medium red in color, its vigorous growth with substantial fruit yield, its day neutral fruiting habit with mid to late season production, its good tolerance to fruit skin damage caused by rain fall, its moderate petiole pubescence, and its tolerance to *Podosphaera leucotricha* (powdery mildew).

2 Drawing Sheets

Botanical classification: *Fragaria×ananassa.*
Variety denomination: 'Verity'.

BACKGROUND OF THE INVENTION

The present invention relates to a new and distinct cultivar of *Fragaria*, botanically known as *Fragaria×ananassa* 'Verity', and will be referred to hereafter by its cultivar name, 'Verity'. 'Verity' is a day-neutral strawberry primarily adapted to the climate and growing conditions of south eastern England and other regions of similar climate and day length.

The new cultivar was derived from an ongoing breeding program conducted by the Inventor at his farm in Kent, United Kingdom. 'Verity' arose from a controlled cross made by the Inventor in 2006 between the cultivar 'Evita' (U.S. Plant Pat. No. 9,091), as the female parent and an unnamed plant from the Inventors breeding program, designated as accession number '04AA21' as the male parent. 'Verity', designated as accession number '06HN43', was selected as a single unique plant in summer 2006 from amongst the seedlings that resulted from the above cross.

Asexual propagation of the new cultivar was first accomplished by rooting of stolons by the Inventor in Kent, United Kingdom in 2006. Asexual propagation by rooting of stolons has shown that the unique characteristics of the new cultivar are stable and reproduced true to type in successive generations.

BRIEF SUMMARY OF THE INVENTION

The following traits have been repeatedly observed and are determined to be characteristics of the new cultivar of strawberry. These attributes in combination distinguish 'Verity' as unique from all other strawberry cultivars known to the Inventor. 'Verity' is well adapted for the growing conditions in the United Kingdom.

1. 'Verity' exhibits an upright dense growth habit.
2. 'Verity' exhibits ovoid shaped berries that are uniformly large in size.

3. 'Verity' exhibits berries with firm skin and juicy, soft flesh.
4. 'Verity' exhibits berries that are glossy and bright medium red in color with color retained throughout production.
5. 'Verity' exhibits vigorous growth with substantial fruit yields.
6. 'Verity' exhibits a day neutral fruiting habit with mid to late season production.
7. 'Verity' exhibits tolerance to fruit skin damage caused by rainfall.
8. 'Verity' exhibits moderate petiole pubescence.
9. 'Verity' exhibits tolerance to *Podosphaera leucotricha* (powdery mildew).

'Evita', the female parent of 'Verity', differs from 'Verity' in having berries that are conical in shape, lower in acidity, and darker red in color. '04AA21', the male parent of 'Verity', differs from 'Verity', in being highly susceptible to *Phytophthora cactorum* and in having berries that are pale red in color.

'Verity' can be most closely compared to the cultivar 'Sweet Eve' (U.S. Plant Pat. No. 21,380) with the following comparison characteristics observed under United Kingdom growing conditions. 'Verity' produces a larger fruit size than 'Sweet Eve' has a fruit shape that is slightly more ovoid to that of 'Sweet Eve', however they are both uniform, a fruit skin similarly firm but juicier fruit than that of 'Sweet Eve', an increased flower truss length than that of 'Sweet Eve', and a flat calyx position relative to the fruit that is significantly larger than that of 'Sweet Eve'. Furthermore, the fruit of 'Verity' has a better shelf life than that of 'Sweet Eve'. Finally, 'Verity' possesses a refreshing soft and juicy fruit texture compared to the fruit of 'Sweet Eve'.

'Verity' plants exhibit a more vigorous growth habit than that of 'Sweet Eve' and when it is grown in the United Kingdom, the plant size is significantly greater than 'Sweet Eve'.

The leaf size of 'Verity' is medium, but larger than that of 'Sweet Eve', and the leaflets are generally round and almost as wide as long.

The petiole and petiolule lengths of 'Verity' are greater than that of 'Sweet Eve'. Some hair is present on 'Verity' at the base of the petiole and close to the stipules but pubescence is more moderate than that of 'Sweet Eve'. The petiolule pubescence of 'Verity' is moderate, but still considerably less than that of 'Sweet Eve'.

The leaflets of 'Verity' typically possess a slightly round (obtuse) base and tip; however, the leaflets are not symmetrical. In fact, the leaflets of 'Verity' express a very distinctive architecture wherein the distance from the petiolule to the first serration is significantly longer on one side compared to the other (approximately 20%). The serrations express slightly pointed to slightly rounded tips with the leaflets of 'Verity' plants possessing a slightly smaller number of serrations per leaf than that of 'Sweet Eve'. The most outstanding difference between the two varieties is expressed in the leaf architecture, where the leaflets of 'Verity' are flat or slightly convex, whereas the leaflets of 'Sweet Eve' express an upwards curving feature. Many leaflets of 'Verity' exhibit slight to moderate puckering/blistering, a feature that is visible on more mature leaves.

'Verity' flower trusses tend to grow within the foliage that do not stand out of the leaf canopy, however approximately 50% of the overall trusses are exposed over the leaf canopy. These exposed fruit trusses, when loaded with fruit, tend to protrude to the sides of the plant between the leaves rather than expressing a totally upwards direction. The presence of a bract can be seen on 80% of the flower trusses from early developmental stage, which progresses into a typical leaflet as the truss matures and fruit develops.

The primary flowers of 'Verity' are generally larger than those of 'Sweet Eve'. Petal numbers of 'Verity' are similar to 'Sweet Eve'. The calyx of 'Verity' is significantly larger than that of 'Sweet Eve'. The calyxes of 'Verity' are typically flat touching the shoulders of the fruit, however some are recurving expressing a very narrow fruit neck at the top of the berry.

The berries of 'Verity' are large in size with a shape that is predominantly ovoid with broad shoulders. When grown in the United Kingdom, the fruit of 'Verity' has an even uniform shape without a neck, feature that is very prominent in the fruit of 'Sweet Eve'.

'Verity' berries are darker than those of 'Sweet Eve'. During the summer season, the fruit of 'Verity' retains its bright red color and appears to be unaffected by the higher seasonal temperatures. 'Verity' has shown to exhibit significant tolerance to the effect of rain splitting the fruit skin.

The achenes of 'Verity' berries are characterized as being generally even to slightly indented into the surface of the fruit, however, this indentation is less dramatic when compared to the achenes of 'Sweet Eve'. 'Verity' berries generally contain fewer achenes than those of 'Sweet Eve'.

The berries of 'Verity' are noticeably juicier than 'Sweet Eve' throughout the cropping season with a pleasant combination of flavor, sugar, and low acid levels. The berry skin of 'Verity' is firmer than that of 'Sweet Eve' and resists bruising better during rubbing than the latter. The fruit flesh of 'Verity' is less firm than that of 'Sweet Eve' resulting in a soft and juicy texture and a nice eating experience.

BRIEF DESCRIPTION OF THE DRAWINGS

The accompanying colored photographs illustrate the overall appearance and distinct characteristics of the new *Fragaria*. The photographs were taken of five month-old plants of 'Verity' as grown outdoors in field trials with tunnels and polyethylene covers in Kent, The United Kingdom.

The photograph in FIG. 1 provides a view of the dense plant habit of 'Verity' with flowers and fruit in various stages of development.

Figure 1:
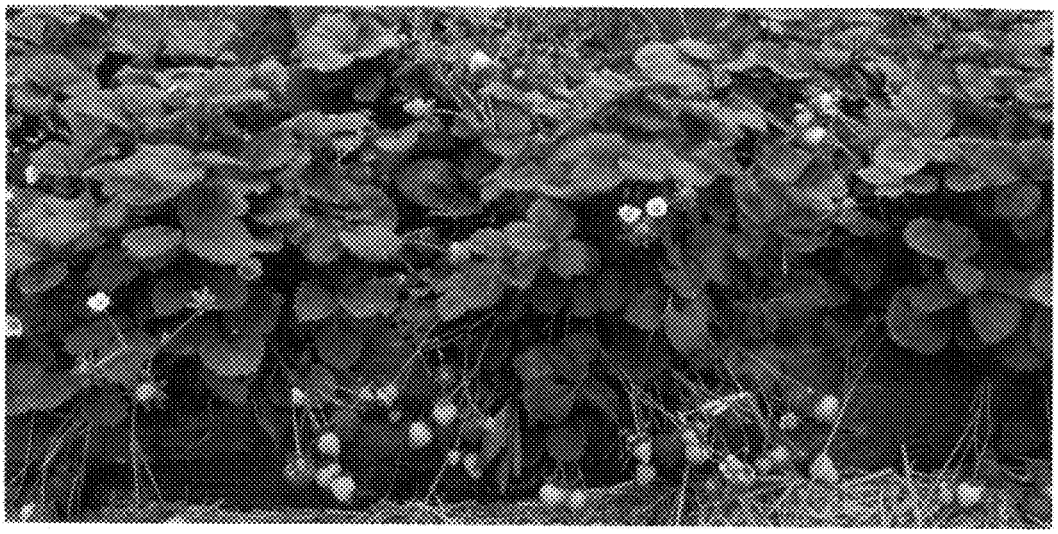
Figure 2:
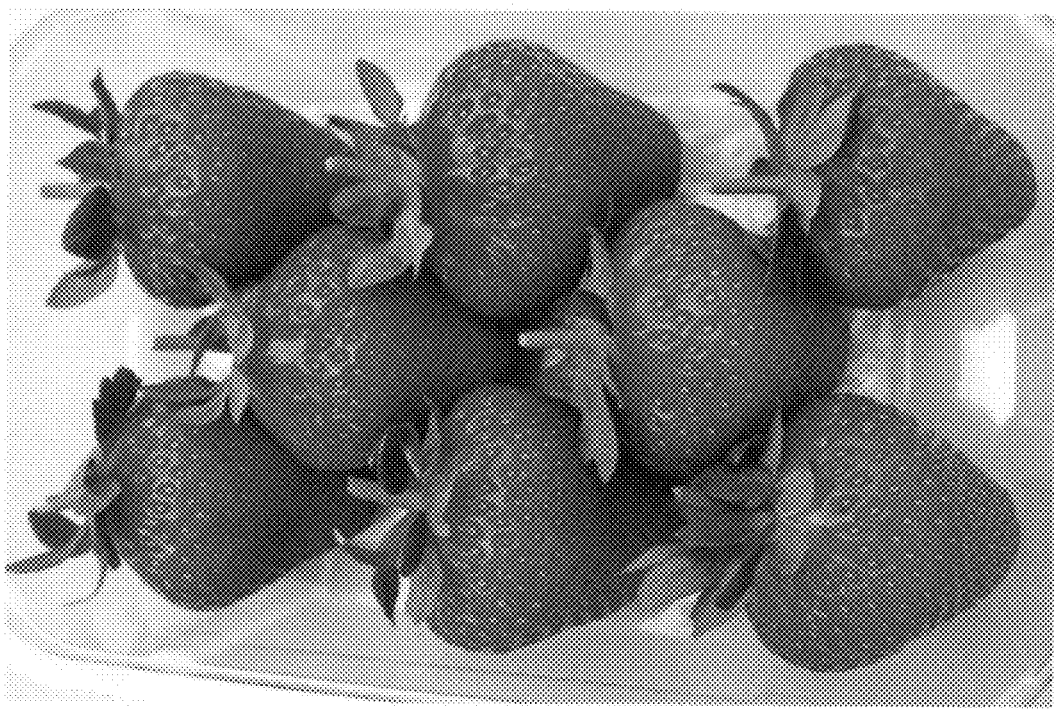

The photograph in FIG. 2 provides a close-up view of the berries of 'Verity'.

Figure 3:
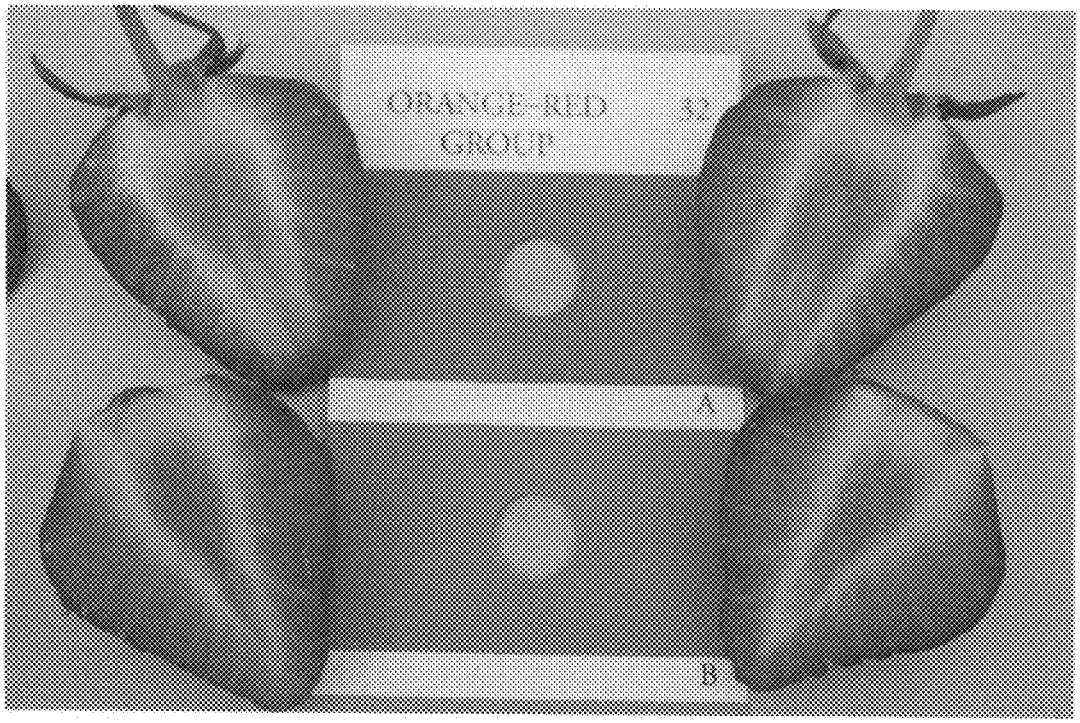

The photograph in FIG. 3 provides a close-up view of the berry flesh of 'Verity'.

Figure 4:
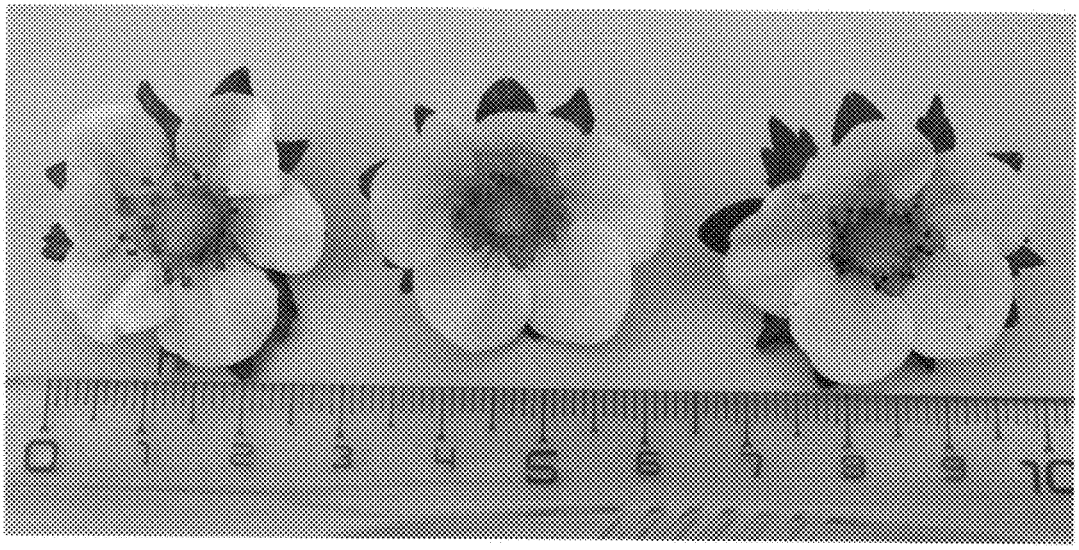

The photograph in FIG. 4 provides a close-up view of the flowers of 'Verity'.

The photographs depict color features as true as is reasonably possible with the digital photography methods used and the color values cited in the detailed botanical description accurately describe the new *Fragaria*.

DETAILED BOTANICAL DESCRIPTION

The following is a detailed description of five month-old plants of 'Verity' as grown in trial fields with tunnels and polyethylene covers in Kent, The United Kingdom. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

- *Blooming period*.—Mid-June through September in Kent, The United Kingdom.
- *Plant type*.—Herbaceous fruit producing perennial.
- *Plant habit*.—Upright with dense canopy.
- *Height and spread*.—Large; reaches an average of 38.8 cm in height and 50.2 cm in width.
- *Cold hardiness*.—At least to U.S.D.A. Zone 5.
- *Environmental stresses*.—Berries have shown to be resistant to rain damage.
- *Diseases resistance*.—Tolerance to *Podosphaera leucotricha* (powdery mildew) has been observed.
- *Root description*.—Fibrous.
- *Propagation*.—Rooting of stolons.
- *Growth rate*.—Vigorous.
- *Stem description*.—Acaulescent.
- *Stolon description*.—An average of 50 cm in length and 2.5 mm in length, 158A In color and flushed with 63D.

Foliage description:

- *Leaf division*.—Three leaflets.
- *Leaf arrangement*.—Basal.
- *Leaf attachment*.—Petiolate.
- *Leaflet shape*.—Broadly ovate to rounded.
- *Mid-tier leaflet size*.—Average of 11.9 cm in length and 11.8 cm in width.
- *Leaflet margins*.—Serrate, slightly pointed to slightly rounded, an average of 16.8 serrations per leaf.
- *Angle of terminal leaflet to petiole*.—30 degrees from vertical.
- *Leaflet base*.—Asymmetrically oblique.
- *Leaflet apex*.—Round.
- *Leaflet profile*.—Flat to slightly convex.
- *Leaflet interveinal blistering*.—Slight to moderate.
- *Leaflet venation*.—Pinnate, upper surface; 137A, lower surface; between 145A and 145B.

*Leaflet aspect*.—Flat to slightly convex.

*Leaflet surface*.—Both surfaces glabrous with slight to moderate blistering depending on leaf age.

*Leaflet color*.—Upper surface 137A, lower surface 138A to 138B.

*Petiole*.—Round in shape, average of 35.2 cm in length and 5 mm in width, moderately pubescent surface, 145A in color.

*Petiolules*.—Round in shape, average of 12 mm in length and 2 mm in width, moderately pubescent surface, 145AC in color.

*Stipule*.—Average of 1.2 cm in length and 3.3 cm in width, 65A in color (weak to moderate anthocyanin).

Flower description:

*Inflorescence*.—Truss.

*Inflorescence length*.—Medium to long; average of 28 cm.

*Flower initiation and expression conditions*.—Temperature dependent and day-length independent.

*Time of flowering* (50% *of plants at first flower*).—Medium to late.

*Number of flowers per truss*.—Average of 7.

*Flower position relative to foliage*.—Mostly even with some exposed above.

*Flower diameter*.—Average of 3.1 cm.

*Calyx*.—Position even, average of 4.6 cm in diameter, larger than corolla.

*Sepals*.—Average of 10, oblong to oblanceolate, an average of 9 mm in length and 5 mm in width, 138A and 138B on upper surface, 137A on lower surface, truncate base, acuminate to acute apex, slightly pubescence surface on upper and lower surface.

*Petals*.—5 to 6, average of 1.2 cm in length and 1.3 cm in width, round in shape, obtuse base and apex, slightly overlapping, entire margins, upper and lower surface glabrous and 155C in color.

*Peduncle*.—137B in color, moderately pubescent surface, average of 2 cm in length and 3 mm in width.

*Pedicel*.—150D in color, pubescent surface, average of 4 cm in length and 1.5 mm in diameter.

*Pistils*.—Average of 140, average of 1.1 mm in length, 151C in color.

*Stamens*.—Average of 21, average of 2.5 mm in length, anther 162D in color, filaments 150B in color, pollen 200B in color.

Fruit description:

*Shape*.—Ovoid with broad shoulders, shape is similar for primary, secondary and tertiary fruit.

*Season of harvest*.—Mid-June bearing through September in Kent, The United Kingdom.

*Time of ripening* (50% *of plants with first ripe fruit*).—Medium to late.

*Type of bearing*.—Day-neutral.

*Size*.—Large; an average of 4.4 cm in length and 4.0 cm in width.

*Surface*.—Smooth and glossy.

*Calyx position*.—Even to very slightly raised and recurved.

*Attitude of calyx segments*.—Some recurved, others touching fruit shoulder.

*Diameter of calyx relative to fruit diameter*.—Smaller.

*Glossiness*.—Even and high.

*External color* (*skin*).—44A.

*Internal color* (*flesh*).—32B and 32A near edges.

*Evenness of color of skin*.—Very even.

*Evenness of color of flesh*.—Even.

*Acidity*.—Moderate.

*Sweetness*.—Medium to high.

*Soluble solids*.—9.3.

*Firmness*.—Skin is firm, flesh is moderately firm.

*Juiciness*.—High.

*Aroma*.—Moderate.

*Weight*.—Average of 32 g per berry and 1,380 g per plant in a harvest season.

*Hollow center*.—Weakly expressed or not present on primary fruit, not present on secondary and tertiary fruit.

*Shelf life*.—Long.

*Achene color*.—12A.

*Achene position*.—Even to slightly indented.

*Achene number*.—An average of 302 per berry.

*Band within achenes*.—Narrow.

It is claimed:

1. A new and distinct cultivar of strawberry plant named 'Verity' as herein illustrated and described.

* * * * *